US009435792B2

(12) United States Patent
Shen et al.

(10) Patent No.: US 9,435,792 B2
(45) Date of Patent: Sep. 6, 2016

(54) HEMOLYSIS REAGENT COMPOSITION FOR HEMOGLOBIN A1C QUANTITATIVE ANALYSIS USING ENZYMATIC METHOD

(71) Applicant: I-Sens, Inc., Seoul (KR)

(72) Inventors: Dongxuan Shen, Seoul (KR); Joo Young Cho, Gyeonggi-do (KR); Kap Soo Park, Gyeonggi-do (KR); Geun Sig Cha, Seoul (KR); Hakhyun Nam, Seoul (KR)

(73) Assignee: I-SENS, INC., Seoul (KR)

( * ) Notice: Subject to any disclaimer, the term of this patent is extended or adjusted under 35 U.S.C. 154(b) by 117 days.

(21) Appl. No.: 14/373,977

(22) PCT Filed: Nov. 16, 2012

(86) PCT No.: PCT/KR2012/009715
§ 371 (c)(1),
(2) Date: Jul. 23, 2014

(87) PCT Pub. No.: WO2013/118960
PCT Pub. Date: Aug. 15, 2013

(65) Prior Publication Data
US 2014/0370539 A1    Dec. 18, 2014

(30) Foreign Application Priority Data

Feb. 10, 2012   (KR) .................. 10-2012-0013841

(51) Int. Cl.
*C12Q 1/26* (2006.01)
*G01N 33/50* (2006.01)
*C07C 309/14* (2006.01)
*G01N 33/72* (2006.01)

(52) U.S. Cl.
CPC ......... *G01N 33/5091* (2013.01); *C07C 309/14* (2013.01); *C12Q 1/26* (2013.01); *G01N 33/721* (2013.01); *G01N 2333/805* (2013.01)

(58) Field of Classification Search
None
See application file for complete search history.

(56) References Cited

U.S. PATENT DOCUMENTS

| 5,541,117 A | 7/1996 | Karl et al. ................ 436/518 |
| 5,858,794 A | 1/1999 | Malin ........................ 436/66 |
| 7,070,948 B1 | 7/2006 | Sakaue et al. ............. 435/23 |
| 2003/0044995 A1* | 3/2003 | Merabet .............. G01N 33/721 436/66 |
| 2003/0444995 | 3/2003 | Merabet et al. .......... 436/66 |
| 2005/0221415 A1 | 10/2005 | Yonehara et al. ........ 435/25 |
| 2012/0003678 A1* | 1/2012 | Aisaka ................ C07K 14/805 435/23 |

FOREIGN PATENT DOCUMENTS

| JP | 1993-192193 A | 8/1993 |
| JP | 1998-319021 A | 12/1998 |
| JP | 2001-095598 A | 4/2001 |
| JP | 2007-147630 A | 6/2007 |
| WO | WO02/21142 A1 | 3/2002 |

OTHER PUBLICATIONS

GbioSciences, Geno Technology, 2009, 2 pages.*
Calbiochem, "Biological Detergents", Calbiochem, CB0733, 2006, 12 pages.*
International Search Report from PCT/KR2012/09715, Mar. 28, 2013, PCT.

* cited by examiner

Primary Examiner — Louise W Humphrey
Assistant Examiner — Aaron J Kosar
(74) Attorney, Agent, or Firm — Licata & Tyrrell P.C.

(57) ABSTRACT

Disclosed is a hemolysis reagent composition for the quantitative analysis of glycated hemoglobin (HbA1c) via an enzymatic method. The hemolysis reagent compositions of the present invention containing a zwitterionic surfactant and a nitrous compound considerably accelerate hemolysis rate due to the presence of the zwitterionic surfactant, and also induce the N-terminal β-chain of hemoglobin released by hemolysis to be exposed to the outside of the hemoglobin molecule and assists the participation of a greater number of molecules in the reaction, thereby improving reaction sensitivity and reaction rate of the glycated hemoglobin, and the nitrous compound makes the protein structure of the hemoglobin flexibly modified so that the amino acid sequence of the N-terminal β-chain of hemoglobin can be readily cut off, thereby significantly reducing the entire time required for the measurement and improving the accuracy of the measurement.

9 Claims, 8 Drawing Sheets

HEMOLYSIS REAGENT COMPOSITION FOR HEMOGLOBIN A1C QUANTITATIVE ANALYSIS USING ENZYMATIC METHOD

This patent application is the National Stage of International Application No. PCT/KR2012/009715 filed Nov. 16, 2012, which claims the benefit of priority from Korean Application No. 10-2012-0013841, filed Feb. 10, 2012, each of which are herein incorporated by reference in their entirety.

TECHNICAL FIELD

The present disclosure relates to a novel hemolysis reagent composition for quantitative analysis of glycated hemoglobin using an enzymatic method.

BACKGROUND ART

Recently, there has been a growing concern on the necessity of a periodic checkup on the blood glucose level for the diagnosis and prevention of diabetes. The blood glucose level can be easily measured using a portable blood glucose monitoring device, in particular, using a strip type biosensor by each individual.

However, it is inconvenient to use because the results of blood glucose measurements varies depending on whether a patient has taken a meal or not, and the measured value may vary depending on the patient's physical conditions on the examination day, e.g., stress, drinking, fatigue, etc.

In contrast, when a diabetic patient is measured and managed using glycated hemoglobin (HbA1c), the result is not affected by factors such as physical conditions of the patient or whether the patient has taken a meal or not. It is generally accepted that HbA1c value reflects the average blood glucose level for a period of about 3 to 4 months, and thus can be used as an index for evaluating the efficiency of the patient's method of managing the blood glucose level. This is because the glucose present in blood reacts with hemoglobin, the blood constituting protein, for a long period of time, undergoes the Amadori rearrangement, and forms a modified protein of hemoglobin-glucose, the so-called glycated hemoglobin (HbA1c). The structure of the HbA1c is shown below.

Since the life cycle of the thus formed HbA1c is about from 90 to 120 days, it can provide a very important data for the diagnosis of diabetes of a patient or the efficiency of blood glucose management by the patient based on the average blood glucose level.

The clinical evaluation of the HbA1c is measured by the HbA1c's relative ratio to the total hemoglobin concentration in terms of percentage. The HbA1c value of 6.0% or less is considered normal. The HbA1c value is a very important factor in managing diabetes complications. According to reports, for example, when the HbA1c value is lowered by 1% it has the effects of reducing the risk of myocardial infarction by 14%, cataract by 19%, microangiopathy by 37%, peripheral arterial disease by 43%, death from diabetes by 21%, etc.

Although routine measurement of a patient's blood glucose level is important to check the patient's daily health conditions and provide an appropriate treatment for the patient accordingly, it is still necessary to measure the patient's glycated protein or HbA1c level in order to determine the patient's long-term blood glucose management status, prevent complications, and provide a suitable treatment for the patient.

A standard method of measuring the HbA1c level in blood, which serves as an important index in blood glucose management, may include hemolyzing a collected blood sample by mixing it with a suitable reagent, e.g., a surfactant such as TX-100, passing it through an HPLC ion-exchange or affinity column packed with beads/gels with a functional surface of boronic acid derivatives, measuring particular wavelength of proteins separated therefrom via visible light apart from normal proteins, thereby calculating the ratio of glycated proteins.

However, the standard method described above has a disadvantage that it can be only performed in a well-facilitated major clinical laboratory or a hospital's central laboratory by a trained clinical professional and the operation and maintenance is relatively costly, esp. when fewer tests are ordered. Additionally, the blood HbA1c level may be measured using HbA1c antibodies. However, the amount of the supplies is very limited due to the lack of companies producing the same, and also the apparatus is very complicated requiring a reaction-separation step.

U.S. Pat. No. 5,541,117 discloses a method for determining hemoglobin content via reflectance photometry after preparing a pad on which antibodies are coupled and allowing a blood sample to be hemolyzed and introduced onto the pad. However, its drawbacks include using high cost antibodies, and having a difficulty in manufacturing sensors with uniform quality due to non-uniformity in porous pads. Additionally, the relative amount of the glycated protein is determined electrochemically using a marker compound after separating proteins in the sample via an antibody modified solid phase. However, glycated proteins and glycated protein-marker complex competitively gather around the surface of electrodes and signals from the electrochemical reactions between the marker and injected substrate is largely inhibited. Therefore the measurement of glycated proteins is compromised and performance with regard to reproducibility is undermined.

As an alternative, an enzymatic method may be used to measure the concentration of a glycated protein such as HbA1c. The enzymatic method includes introducing a protease to the glycated protein of a given sample, performing a pretreatment to release the glycated peptides or glycated amino acids, which are used as a substrate for the following reaction, where an intermediate product (e.g., hydrogen peroxide) is produced by acting a glycated peptide-specific enzyme or glycated amino acid-specific enzyme (e.g., fructosyl peptide oxidase or fructosyl amino acid oxidase) on the separated substrate, and followed by a signal-producing peroxidase-hydrogen peroxide reaction with an appropriate color developing agent, e.g. a detectable product.

Japanese Patent Application Publication No. H5-192193 discloses a method for a specific quantification of fructosamine by specifically recognizing the ketoamine structure present in fructosamine, separating ketoamine oxydase, which is a novel enzyme catalyzing the oxidation of the ketoamine structure, from various microorganisms, oxidizing only the fructosamine pretreated with a protease in the presence of the ketoamineoxidase, and measuring the resulting product, i.e., glucosone or hydrogen peroxide.

Japanese Patent Application Publication No. 2001-95598 discloses a method for measuring hydrogen peroxide formed by treating a glycated protein-containing sample with a protease, separating a glycated peptide, preferably an α-glycated peptide, more preferably an α-glycated dipeptide, from the glycated protein, and then acting oxydase on the separated glycated peptide, or a method of measuring the separated glycated peptide via HPLC, and also discloses a method of measuring the glycated peptide in a given sample, and a reagent kit for the measurement via an enzymatic method.

HbA1c is a compound in which glucose is bound to a valine residue of N-terminal β chain of hemoglobin A (HbA) (α2β2), and the degree of glycation is indicated in terms of percentage (%) or mmol of HbA1c concentration relative to the total hemoglobin concentration (mole). According to the enzymatic method of the present invention, N-terminal β chain of hemoglobin to which glucose is bound should be converted into monomeric substances of fructocyl amino acid by a protein-digesting protease. The thus formed fructocyl amino acid reacts with fructocyl peptide oxidase (FPOX), an oxidase, to generate hydrogen peroxide, and the hydrogen peroxide generated thereof is oxidized by peroxidase (POD), and the concentration of the HbA1c is measured by analyzing the degree of color development of a substrate through a reduction caused by electrons released by the oxidation via a spectrophotometric analysis.

The enzymatic method using various enzymes as described above has an advantage that it can provide a more accurate result due to the enzyme's characteristic of selectivity compared to other methods, but it has a disadvantage that it requires a long reaction time and its reaction sensitivity is low due to sophisticated reaction conditions.

The inventors of the present invention, while endeavoring to find a method to improve reaction rate and reaction sensitivity in the enzymatic method for the quantification of HbA1c, discovered that when a Zwitterionic surfactant and a nitrous compound containing reagent composition is added to a hemolysis reagent, it considerably accelerates the hemolysis rate and also induces the N-terminal β-chain of hemoglobin released by hemolysis to be exposed to the outside of the hemoglobin molecule and assists the participation of a greater number of molecules thereby improving reaction sensitivity and reaction rate of the HbA1c, and the nitrous compound makes the protein structure of the hemoglobin flexible so that the amino acid sequence of the N-terminal β-chain of hemoglobin can be readily cleaved off, thereby significantly reducing the entire time required for the measurement and improving the accuracy of the measurement, thus completing the present invention.

DISCLOSURE OF THE INVENTION

Technical Problem

One object of the present invention is to provide a hemolysis reagent composition which can reduce the time required for measurement by accelerating a reaction, rate and also increase reaction sensitivity by maximizing reaction signal in the method of measuring the concentration of HbA1c using a conventional enzymatic method.

Another object of the present invention is to provide a method for quantitative analysis of HbA1c using the hemolysis reagent composition.

Technical Solution

In order to achieve the objects, the present invention provides a hemolysis reagent composition used in a pretreatment process of quantitative analysis of HbA1c via an enzymatic method containing a zwitterionic surfactant, represented by the Chemical Formula 1 below, and a nitrous compound:

[Chemical Formula 1]

wherein $R^1$ and $R^2$ are independently a linear or branched $C_{1-5}$ alkyl, respectively;

n is an integer from 1 to 6;

X is a single bond or wherein when X is m is an integer from 1 to 3, $R^3$ is a $C_{13}$ linear or branched alkyl, and when X is a single bond m is 1, $R^3$ is a $C_{13}$ linear or branched alkyl.

The present invention also provides a method for quantitative analysis of HbA1c, including:

hemolyzing red blood cells using the hemolysis reagent composition of claim 1 (step 1);

measuring the total amount of hemoglobin released by the hemolysis of the red blood cells in step 1 (step 2);

obtaining monomeric fructosyl amino acids by selectively cutting off only the 'sugar-val-his-' moiety of the N-terminal β-chain of the HbA1c released by the hemolysis of the red blood cells in step 1 using a protease (step 3);

producing hydrogen peroxide by reacting fructosyl peptide oxidase (FPOX) with the fructosyl amino acids obtained in step 3 (step 4);

oxidizing the hydrogen peroxide produced in step 4 by reacting with peroxidase (POD) (step 5);

measuring the amount of color development induced by a redox reaction due to the hydrogen peroxide oxidized in step 5 and a substrate (step 6); and quantitating the concentration of the HbA1c in a blood sample by comparing the total amount of hemoglobin measured in step 2 and the amount of the HbA1c in step 6.

Advantageous Effects

The hemolysis reagent composition of the present invention containing a zwitterionic surfactant and a nitrous compound considerably accelerates hemolysis rate due to the presence of the zwitterionic surfactant, and also induces the N-terminal β-chain of hemoglobin released by hemolysis to be exposed to the outside of the hemoglobin molecule and assists the participation of a greater number of molecules thereby improving reaction sensitivity and reaction rate of the HbA1c, and the nitrous compound makes the protein structure of the hemoglobin flexible so that the amino acid sequence of the N-terminal β-chain of hemoglobin can be readily cut off, thereby significantly reducing the entire time required for the measurement and improving the accuracy of the measurement.

BEST MODE FOR CARRYING OUT THE INVENTION

The present invention relates to the measurement of a relative concentration of HbA1c with reference to the concentration of the total hemoglobin. In particular, the present invention aims at improving the sensitivity of measuring the total hemoglobin and HbA1c and also reducing the time required for the measurement using an improved hemolysis reagent composition.

For the measurement of a relative concentration it is essential that both values of the total hemoglobin and the HbA1c be measured. Here, the hemoglobin value may be measured using a spectroscopic device such as UV/Vis, considering that the hemoglobin released out of red blood cells during hemolysis, performed as a pretreatment for quantification of HbA1c via enzymatic method, shows characteristic spectroscopic peaks at a region near 530 nm. Additionally, as described in Background Art, the value of HbA1c may be measured by subjecting the blood sample which went through with hemolysis to enzymatic reactions utilizing a protease, FPOX, POD and a substrate.

The present invention is described in greater details herein below.

The present invention provides a hemolysis reagent composition used in a pretreatment process of quantitative analysis of glycated hemoglobin via an enzymatic method containing a zwitterionic surfactant, represented by the Chemical Formula 1 below, and a nitrous compound:

[Chemical Formula 1]

wherein $R^1$ and $R^2$ are independently a linear or branched $C_{1-5}$ alkyl, respectively;
n is an integer from 1 to 6;
X is a single bond or wherein when X is m is an integer from 1 to 3, $R^3$ is a $C_{13}$ linear or branched alkyl, and when X is a single bond m is 1, $R^3$ is a $C_{13}$ linear or branched alkyl.

Preferably,

$R^1$ and $R^2$ are independently a linear or branched $C_{1-3}$ alkyl, respectively;

n is an integer from 1 to 4;

X is a single bond or wherein when X is m is an integer from 1 to 3, $R^3$ is a $C_{13}$ linear or branched alkyl, and when X is a single bond m is 1, $R^3$ is a $C_{13}$ linear or branched alkyl.

More preferably, the zwitterionic surfactant represented by the Chemical Formula 1 is:

3-(dimethyl(3-tetradecanamidopropyl)ammonio)propane-1-sulfonate;

4-(dimethyl(3-tetradecanamidopropyl)ammonio)butane-1-sulfonate; or 3-(dimethyl(tetradecyl)ammonio)propane-1-sulfonate.

Referring to the reagent composition according to the present invention, the zwitterionic surfactant, represented by the Chemical Formula 1, serves to accelerate hemolysis rate, softens the structure of hemoglobin, and improve the activities of enzymatic reactions after the pretreatment. The enzymatic reactions after the pretreatment will be described in the method of quantitative analysis of HbA1c using the enzymatic method shown below.

Preferably, the zwitterionic surfactant is added in the amount of from 0.5 to 1.0 wt %. When the zwitterionic surfactant is added less than 0.5 wt % it will decrease the hemolysis reaction rate or no hemolysis may occur at all. In contrast, when the zwitterionic surfactant is added more than 1.0 wt % it reduces hemolysis reaction sensitivity.

Regarding the reagent composition of the present invention, the nitrous compound not only mediates an easy analysis of the total hemoglobin, as known in the related art, but also flexibilizes the hemoglobin structure, and therefore helps a protease to selectively cut down only the 'sugar-Val-His-' moiety of N-terminal β-chain to thereby obtain monomeric fructosyl amino acid after the pretreatment.

As for the nitrous compound, sodium nitrite, potassium nitrite, magnesium nitrite, calcium nitrite, etc., may be used alone or in combination thereof.

Preferably, the nitrous compound is added to be in the range of from 1 to 5 mM. When the concentration of the nitrous compound is below 1 mM the hemoglobin structure may not be sufficiently modified to a flexible structure, whereas when the concentration of the nitrous compound is above 5 mM there may occur scattering at the time of measuring the concentration of the total hemoglobin.

Additionally, the present invention also provides a method for quantitative analysis of HbA1c, including:

hemolyzing red blood cells using the hemolysis reagent composition (step 1);

measuring the total amount of hemoglobin released by the hemolysis of the red blood cells in step 1 (step 2);

obtaining monomeric fructosyl amino acids by selectively cutting off only the 'sugar-Val-His-' moiety of the N-terminal β-chain of the HbA1c released during the hemolysis of the red blood cells in step 1 using a protease (step 3);

producing hydrogen peroxide by reacting fructosyl peptide oxidase (FPOX) with the fructosyl amino acids obtained in step 3 (step 4);

oxidizing the hydrogen peroxide produced in step 4 by reacting with peroxidase (POD) (step 5);

measuring the amount of color development induced by a redox reaction due to the hydrogen peroxide oxidized in step 5 and a substrate (step 6); and quantitating the concentration of the glycated hemoglobin in a blood sample by comparing the total amount of hemoglobin measured in step 2 and the amount of the glycated hemoglobin in step 6.

The method for quantitative analysis of HbA1c using the enzymatic method of the present invention will be stepwisely described in detail herein below.

In the quantitative analysis of the present invention, step 1 relates to a pretreatment process wherein red blood cells are hemolyzed using a hemolysis reagent composition including a zwitterionic surfactant represented by the Chemical Formula 1 and a nitrous compound.

In particular, the zwitterionic surfactant represented by the Chemical Formula 1 flexibilizes the hemoglobin structure and at the same time improves the activities of enzyme reaction after step 1.

Preferably, the zwitterionic surfactant is added in the range of from 0.5 to 1.0 wt %. When the zwitterionic surfactant is added less than 0.5 wt % it may decrease the rate of hemolytic reaction or no hemolysis may occur. In contrast, when the zwitterionic surfactant is added more than 1.0 wt % it will reduce the sensitivity of hemolytic reaction.

The nitrous compound not only mediates an easy analysis of the total hemoglobin, as known in the related art, but also flexibilizes the hemoglobin structure, and therefore helps a protease to selectively cut down only the 'sugar-Val-His-' moiety of N-terminal β-chain to thereby obtain monomeric fructosyl amino acids after the pretreatment.

As for the nitrous compound, sodium nitrite, potassium nitrite, magnesium nitrite, calcium nitrite, etc., may be used alone or in combination thereof.

Preferably, the nitrous compound is added to be in the range of from 1 to 5 mM. When the concentration of the nitrous compound is below 1 mM the hemoglobin structure may not be sufficiently modified to a flexible structure, whereas when the concentration of the nitrous compound is above 5 mM there may occur scattering at the time of measuring the concentration of the total hemoglobin.

In the quantitative analysis of the present invention, step 2 relates to measurement of the amount of the total hemoglobin released out of red blood cells during hemolysis in step 1 above.

More specifically, the hemoglobin value may be measured using a spectroscopic device such as a UV/Vis, considering that the hemoglobin released out of red blood cells during hemolysis, performed as a pretreatment for quantification of HbA1c via enzymatic method, shows characteristic spectroscopic peaks at a region near 530 nm.

In the quantitative analysis of the present invention, step 3 relates to obtaining monomeric fructosyl amino acids by selectively cutting off only the 'sugar-Val-His-' moiety of the N-terminal β-chain of the HbA1c released during the hemolysis of the red blood cells in step 1 using a protease.

The protease to be used may include those derived from *Bacillus* sp., *Aspergillus* sp., *Streptomyces* sp., and a genetic recombination thereof, and they may be used alone or in combination.

Preferably, the protease may be used in the range of from 500 to 1000 U/mL. When the protease is used less than 500 U/mL the sensitivity of the entire reaction becomes small, whereas when the protease is used more than 1000 U/mL it also decomposes the enzyme used along with it thus deteriorating its reactivity.

In the quantitative analysis of the present invention, step 4 relates to formation of hydrogen peroxide ($H_2O_2$) by reacting the fructosyl amino acids obtained in step 3 with fructosyl peptide oxidase (FPOX).

Preferably, FPOX is added in the range of 1.0 U/mL or higher. When FPOX is added in the range of below FPOX 1.0 U/mL the sensitivity of the entire reaction becomes small.

In the quantitative analysis of the present invention, step 5 relates to oxidation of hydrogen peroxide by reacting the hydrogen peroxide obtained in step 4 with peroxidase (POD).

Preferably, POD is added in the range of 5-20 U/mL. When POD is added less than 5 U/mL the sensitivity of the entire reaction becomes small, whereas when POD is added more than 20 U/mL it prevents the measurement of the HbA1c concentration because of its similarity in color to that of hemoglobin.

In the quantitative analysis of the present invention, step 6 relates to measurement of the amount of color development induced through redox reactions by oxidized hydrogen peroxide and a substrate in step 5.

Here, the substrate serves to induce a color development with oxidized hydrogen peroxide generated by the POD via redox reactions, and dyes such as DA-67 and DA-64.

Preferably, the substrate is added in the range of 0.12 mM or less. When the substrate is added exceeding 0.12 mM a spontaneous color change occurs thus causing an error in spectroscopic measurement. Since the substrate is an unstable material changing its color spontaneously according to external environment and temperature, the substrate require a special caution in use.

In the quantitative analysis of the present invention, step 7 relates to quantification of HbA1c concentration among blood samples via relative comparison between the amount of the total hemoglobin measured in step 2 and the amount of HbA1c measured in step 6.

More specifically, the amount of HbA1c may be indicated in percentage by calculation.

Here, the amount of the total hemoglobin in step 2 and the amount of the HbA1c in step 6 may be measured via a spectroscopic apparatus such as a UV/Vis.

As described above, the hemolysis reagent composition of the present invention containing a zwitterionic surfactant and a nitrous compound considerably accelerates hemolysis rate due to the presence of the zwitterionic surfactant, and also induces the N-terminal β-chain of hemoglobin released via hemolysis to be exposed to the outside of the hemoglobin molecule and assists the participation of a greater number of molecules thereby improving reaction sensitivity and reaction rate of the HbA1c, and the nitrous compound makes the protein structure of the hemoglobin flexible so that the amino acid sequence of the N-terminal β-chain of hemoglobin can be readily cut off, thereby significantly reducing the entire time required for the measurement and improving the accuracy of the measurement.

MODE FOR CARRYING OUT THE INVENTION

The present invention will be explained in further detail with reference to Examples below. However, they are given herein below by way of illustration and are thus not limitative of the present invention.

Preparation Example 1

Preparation of an Enzymatic Reaction Composition Used after Pretreatment of Quantitative Analysis of HbA1c A composition for enzymatic reaction used after pretreatment as a hemolysis of quantification of HbA1c was prepared by adding 800 U/mL of a microorganism-derived protease, 1 U/mL of fructosyl peptide oxidase (FPOX), 10 U/mL of peroxidase (POD), and 0.12 mM DA-67 (dye) as a substrate to a 100 mM MES buffer was added.

Example 1

Preparation 1 of a Hemolysis Reagent Composition Used for Pretreatment of Quantitative Analysis of HbA1c A hemolysis reagent composition 1 was prepared by adding 0.75 mg/mL of 3-(dimethyl(3-tetradecanamidopropyl)ammonio)propane-1-sulfonate as a surfactant and 2 mM $NaNO_2$ as a nitrous compound to a 100 mM MES buffer.

Example 2

Preparation 2 of a Hemolysis Reagent Composition Used for Pretreatment of Quantitative Analysis of HbA1c A hemolysis reagent composition 2 was prepared in the same manner as in Example 1 except that 0.75 mg/mL of 4-(dimethyl(3-tetradecanamidopropyl)ammonio)butane-1-sulfonate was used instead of the surfactant used in Example 1.

Example 3

Preparation 3 of a Hemolysis Reagent Composition Used for Pretreatment of Quantitative Analysis of HbA1c A hemolysis reagent composition 3 was prepared in the same manner as in Example 1 except that 0.75 mg/mL of 3-(dimethyl(tetradecyl)ammonio)propane-1-sulfonate was used instead of the surfactant used in Example 1.

Comparative Example 1

Preparation 4 of a Hemolysis Reagent Composition Used for Pretreatment of Quantitative Analysis of HbA1c A hemolysis reagent composition 4 was prepared in the same manner as in Example 1 except that distilled water was used instead of the surfactant used in Example 1.

Comparative Example 2

Preparation 5 of a Hemolysis Reagent Composition Used for Pretreatment of Quantitative Analysis of HbA1c A hemolysis reagent composition 5 was prepared in the same manner as in Example 1 except that 0.75 mg/mL of 2-(6-(dodecyloxy)-4,5-dihydroxy-2-(dihydroxylmethyl)-tetrahydro-2H-pyran-3-yloxy)-6-(hydroxymethyl)-tetrahydro-2H-pyran-3,4,5-triol was used instead of the surfactant used in Example 1.

Comparative Example 3

Preparation 6 of a Hemolysis Reagent Composition Used for Pretreatment of Quantitative Analysis of HbA1c A hemolysis reagent composition 6 was prepared in the same manner as in Example 1 except that 0.75 mg/mL of 4-(dodecyldimethylammonio)butanoate was used instead of the surfactant used in Example 1.

Comparative Example 4

Preparation 7 of a Hemolysis Reagent Composition Used for Pretreatment of Quantitative Analysis of HbA1c A hemolysis reagent composition 7 was prepared in the same manner as in Example 1 except that 0.75 mg/mL of 3-((3-(4-heptylphenyl)-3-hydroxypropyl)dimethylammonio)propane-1-sulfonate was used instead of the surfactant used in Example 1.

Comparative Example 5

Preparation 8 of a Hemolysis Reagent Composition Used for Pretreatment of Quantitative Analysis of HbA1c A hemolysis reagent composition 8 was prepared in the same manner as in Example 1 except that 0.75 mg/mL of 3-(dimethyl(3-palmitamidopropyl)ammonio)propane-1-sulfonate was used instead of the surfactant used in Example 1.

Comparative Example 6

Preparation 9 of a Hemolysis Reagent Composition Used for Pretreatment of Quantitative Analysis of HbA1c A hemolysis reagent composition 9 was prepared in the same manner as in Example 1 except that 0.75 mg/mL of 3-(dimethyl(octyl)ammonio)propane-1-sulfonate was used instead of the surfactant used in Example 1.

Comparative Example 7

Preparation 10 of a Hemolysis Reagent Composition Used for Pretreatment of Quantitative Analysis of HbA1c A hemolysis reagent composition 10 was prepared in the same manner as in Example 1 except that 0.75 mg/mL of 3-(decyldimethylammonio)propane-1-sulfonate was used instead of the surfactant used in Example 1.

Comparative Example 8

Preparation 11 of a Hemolysis Reagent Composition Used for Pretreatment of Quantitative Analysis of HbA1c A hemolysis reagent composition 11 was prepared in the same manner as in Example 1 except that 0.75 mg/mL of 3-(dodecyldimethylammonio)propane-1-sulfonate was used instead of the surfactant used in Example 1.

Comparative Example 9

Preparation 12 of a Hemolysis Reagent Composition Used for Pretreatment of Quantitative Analysis of HbA1c A hemolysis reagent composition 12 was prepared in the same manner as in Example 1 except that 0.75 mg/mL of 3-(hexadecyldimethylammonio)propane-1-sulfonate was used instead of the surfactant used in Example 1.

Comparative Example 10

Preparation 13 of a Hemolysis Reagent Composition Used for Pretreatment of Quantitative Analysis of HbA1c A hemolysis reagent composition 13 was prepared in the same manner as in Example 1 except that 2 mM $NaNO_2$ of a nitrous compound was not used.

The chemical structures of the Zwitterionic surfactants used in Examples 1-3 and Comparative Examples 1-9 are shown in Table 1 below.

TABLE 1

| | Zwitterionic surfactant |
| --- | --- |
| Ex. 1 | 3-(dimethyl(3-tetradecanamidopropyl)ammonio)propane-1-sulfonate |

TABLE 1-continued

| | Zwitterionic surfactant |
|---|---|
| Ex. 2 | <br>4-(dimethyl(3-tetradecanamidopropyl)ammonio)butane-1-sulfonate |
| Ex. 3 | <br>3-(dimethyl(tetradecyl)ammonio)propane-1-sulfonate |
| Comp. Ex. 1 | distilled water |
| Comp. Ex. 2 | <br>2-(6-(dodecyloxy)-4,5-dihydroxy-2-(dihydroxymethyl)-tetrahydro-2H-pyran-3-yloxy)-6-(hydroxymethyl)-tetrahydro-2H-pyran-3,4,5-triol |
| Comp. Ex. 3 | <br>4-(dodecyldimethylammonio)butanoate |
| Comp. Ex. 4 | <br>3-((3-(4-heptylphenyl)-3-hydroxypropyl)dimethylammonio)propane-1-sulfonate |
| Comp. Ex. 5 | <br>3-(dimethyl(3-palmitamidopropyl)ammonio)propane-1-sulfonate |
| Comp. Ex. 6 | <br>3-(dimethyl(octyl)ammonio)propane-1-sulfonate |
| Comp. Ex. 7 | <br>3-(decyldimethylammonio)propane-1-sulfonate |

TABLE 1-continued

| | Zwitterionic surfactant |
|---|---|
| Comp. Ex. 8 | 3-(dodecyldimethylammonio)propane-1-sulfonate |
| Comp. Ex. 9 | 3-(hexadecyldimethylammonio)propane-1-sulfonate |

Experimental Example 1

Evaluation of Solubility of Surfactant

In order to use a surfactant, it is essential that the solubility of a sample itself be excellent. First of all, if the sample is not dissolved it cannot be used at all, and thus the solubility of a surfactant was evaluated as a prerequisite.

More specifically, the solubility of the surfactants used in Examples 1-3 and Comparative Examples 1-9 were dissolved in distilled water to a concentration of 0.75 mg/mL to determine their solubility. The results are shown in Table 2 below.

TABLE 2

| | Solubility |
|---|---|
| Ex. 1 | ○ |
| Ex. 2 | ○ |
| Ex. 3 | ○ |
| Comp. Ex. 1 | ○ |
| Comp. Ex. 2 | ○ |
| Comp. Ex. 3 | ○ |
| Comp. Ex. 4 | ○ |
| Comp. Ex. 5 | ○ |
| Comp. Ex. 6 | ○ |
| Comp. Ex. 7 | ○ |
| Comp. Ex. 8 | ○ |
| Comp. Ex. 9 | x |

As shown in Table 2, it was confirmed that all surfactants except that in Comparative Example 9 were dissolved at a concentration of 0.75 mg/mL, thus being suitable for use in a reagent composition.

According to the result of the above experiment, the hemolysis reagent composition prepared in Comparative Example 9 was excluded from the candidate group for the subsequent experiments.

Experimental Example 2

Evaluation of Hemolysis Rate

The hemolysis rates of the hemolysis reagent compositions prepared in Examples 1-3 and Comparative Examples 1-8 were obtained by the experiments described below.

More specifically, the hemolysis reagent compositions prepared in Examples 1-3 and Comparative Examples 1-8 were reacted with blood for 5 minutes by mixing them in a ratio of 1:400 (blood:hemolysis reagent).

Figure 1:
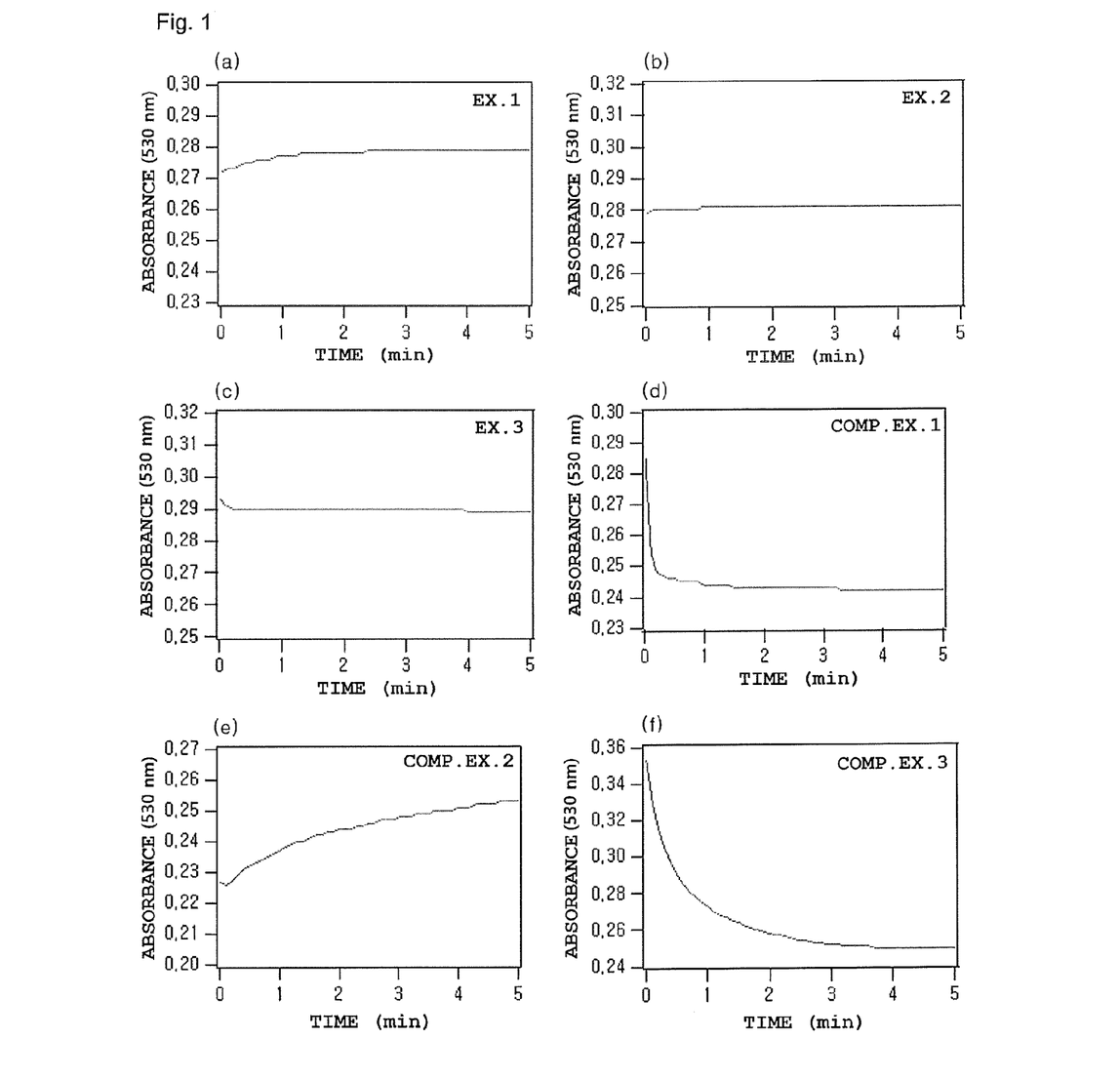
FIGS. 1(a)-1(f) show graphs representing the hemolysis of red blood cells over time passage by the hemolysis reagent composition prepared in Examples 1-3 and Comparative Examples 1-3 of the present invention (in FIG. 1, the change in slope over time passage indicates that the hemolysis of red blood cells is in continued progress, and the region without change in slope indicates the time period during which the hemolysis is terminated).
Figure 2:
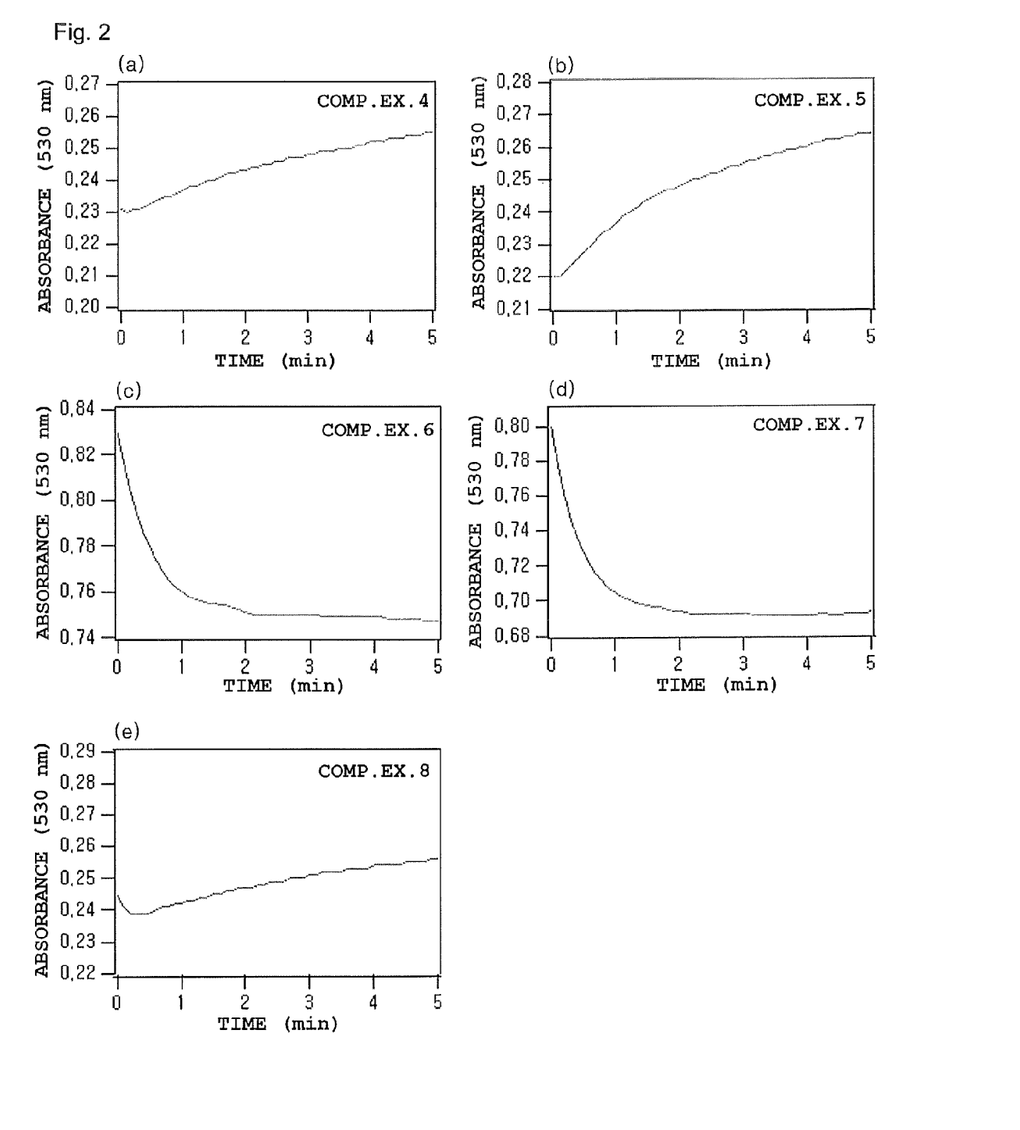
FIGS. 2(a)-2(e) show graphs representing the hemolysis of red blood cells over time passage by the hemolysis reagent composition prepared in Comparative Examples 4-8 of the present invention (in FIG. 2, the change in slope over time passage indicates that the hemolysis of red blood cells is in continued progress, and the region without change in slope indicates the time period during which the hemolysis is terminated).

The absorbance change at 530 nm between 0 and 5 minutes was measured using a UV/Vis apparatus (Model: UV-1800, manufactured by Shimadzu), and the result is shown in FIG. 1, FIG. 2 and Table 3 below.

The values shown in Table 3 below are absolute values obtained by subtracting the value at 30 seconds from the value at 1 minute. If the hemolysis rate is so fast that the hemolysis can be sufficiently completed within 0.5 to 1 minute, the value will be close to 0 and when the reaction is slow the value will be relatively large.

TABLE 3

| | Hemolysis Rate (absorbance at 1 min of reaction-absorbance at 30 seconds of reaction) |
|---|---|
| Ex. 1 | 0.002 |
| Ex. 2 | 0.001 |
| Ex. 3 | 0.000 |
| Comp. Ex. 1 | 0.002 |
| Comp. Ex. 2 | 0.005 |
| Comp. Ex. 3 | 0.017 |
| Comp. Ex. 4 | 0.004 |
| Comp. Ex. 5 | 0.009 |
| Comp. Ex. 6 | scattering |
| Comp. Ex. 7 | scattering |
| Comp. Ex. 8 | 0.003 |

FIG. 1 shows graphs representing the hemolysis of red blood cells over time passage by the hemolysis reagent composition prepared in Examples 1-3 and Comparative Examples 1-3 of the present invention (in FIG. 1, the change in slope over time passage indicates that the hemolysis of red blood cells is in continued progress, and the region without change in slope indicates the time period during which the hemolysis is terminated).

FIG. 2 shows graphs representing the hemolysis of red blood cells over time passage by the hemolysis reagent composition prepared in Comparative Examples 4-8 of the present invention (in FIG. 2, the change in slope over time passage indicates that the hemolysis of red blood cells is in continued progress, and the region without change in slope indicates the time period during which the hemolysis is terminated).

As shown in Table 3 and FIGS. 1-2, the hemolysis reagent compositions prepared in Examples 1-3 exhibited a fast hemolysis rate of less than 1 minute and considering that the change in slope according to time passage indicates the continued hemolytic process of red blood cells, it was confirmed the compositions showed a stable signal with almost no change in slope. In particular, the hemolysis reagent composition prepared in Example 3 showed the fastest hemolysis rate.

According to the result of the above experiment, the hemolysis reagent compositions prepared in Comparative Example 6-7 were excluded from the candidate group for the subsequent experiments.

Experimental Example 3

Evaluation of Reaction Sensitivity of the Total Hemoglobin

In order to measure the relative concentration of the HbA1c via the enzymatic method, it is essential that the concentration of the total hemoglobin be measured together. To this end, it is important to obtain the reaction sensitivity of the total hemoglobin.

To examine the effect of the hemolysis reagent compositions prepared in the present invention on the reaction sensitivity of the total hemoglobin, experiments were performed as follows.

Figure 3:
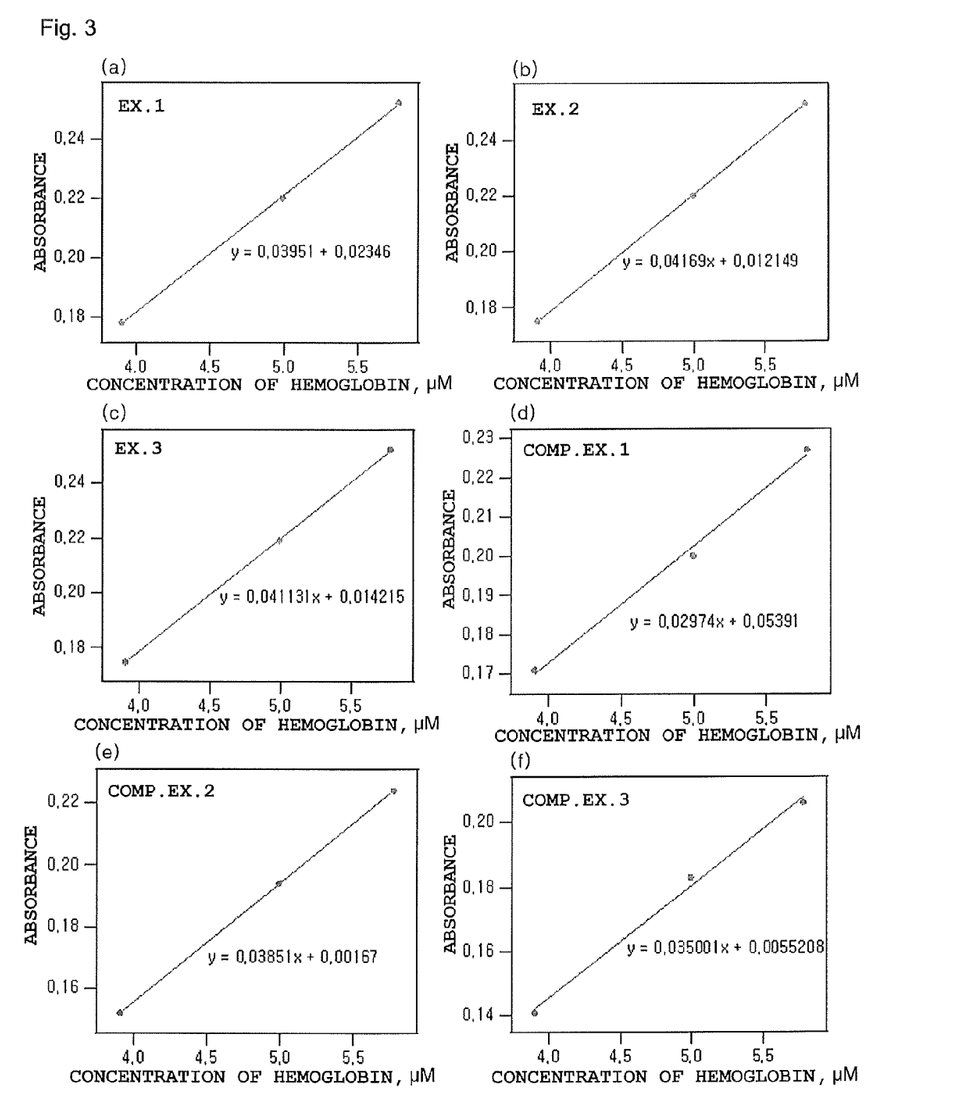
FIGS. 3(a)-3(f) show graphs representing reaction sensitivity of the hemolysis reagent compositions prepared in Examples 1-3 and Comparative Examples 1-3 of the present invention to the total hemoglobin (in FIG. 3, the larger the slope the greater the reaction sensitivity to the total hemoglobin).
Figure 4:
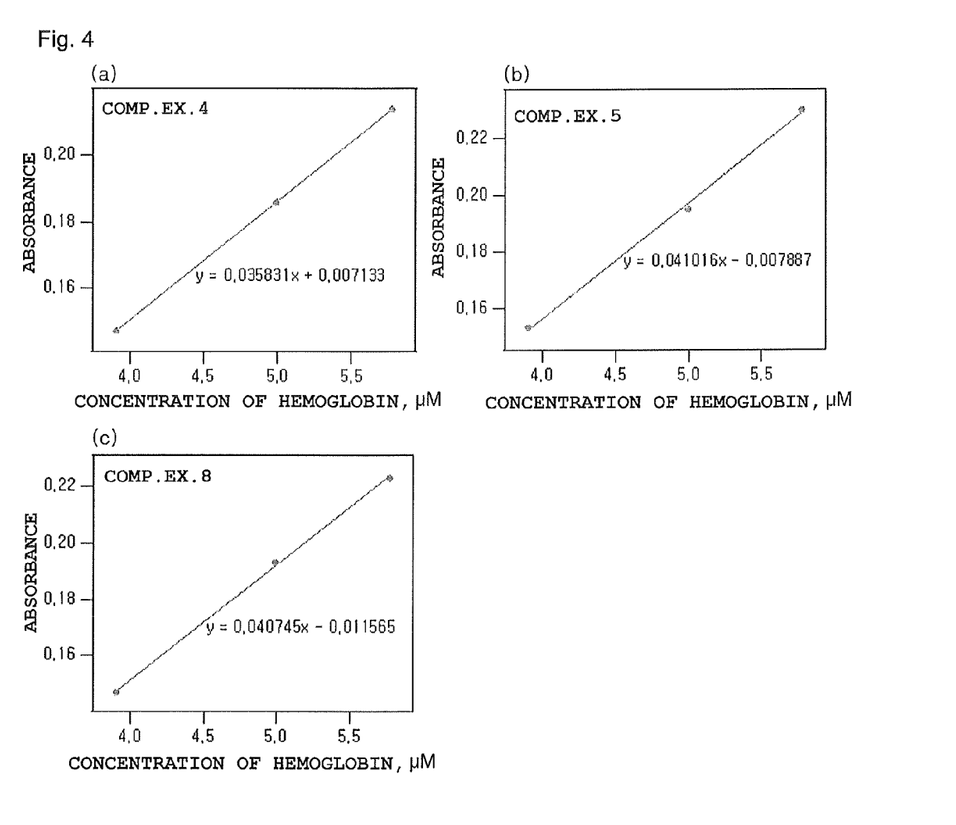
FIGS. 4(a)-4(c) show graphs representing reaction sensitivity of the hemolysis reagent compositions prepared in Comparative Examples 4-5 and 8 of the present invention to the total hemoglobin (in FIG. 3, the larger the slope the greater the reaction sensitivity to the total hemoglobin).

More specifically, three blood samples with different total hemoglobin concentrations (10.5 g/dL, 13.4 g/dL, and 15.6 g/dL) were prepared, and each of the blood samples were respectively reacted with the hemolysis reagent compositions prepared in Examples 1-3, Comparative Examples 1-5 and 8 for 1 minute by mixing them in a ratio of 1:400 (blood:hemolysis reagent), and their absorbances at 530 nm were measured using the same UV/Vis device as in Experimental Example 2, and the results are shown in FIGS. 3-4. Additionally, the slopes of the graphs indicating the reaction sensitivity of the total hemoglobin in FIGS. 3-4 are shown in Table 4 below.

TABLE 4

| | Measurement Sensitivity of Total Hemoglobin |
|---|---|
| Ex. 1 | 0.039510 |
| Ex. 2 | 0.041690 |
| Ex. 3 | 0.041131 |
| Comp. Ex. 1 | 0.029740 |
| Comp. Ex. 2 | 0.038510 |
| Comp. Ex. 3 | 0.035001 |
| Comp. Ex. 4 | 0.035830 |
| Comp. Ex. 5 | 0.041020 |
| Comp. Ex. 8 | 0.040745 |

FIG. 3 shows graphs representing reaction sensitivity of the hemolysis reagent compositions prepared in Examples 1-3 and Comparative Examples 1-3 of the present invention to the total hemoglobin (in FIG. 3, the larger the slope the greater the reaction sensitivity to the total hemoglobin).

FIG. 4 shows graphs representing reaction sensitivity of the hemolysis reagent compositions prepared in Comparative Examples 4-5 and 8 of the present invention to the total hemoglobin (in FIG. 4, the larger the slope the greater the reaction sensitivity to the total hemoglobin).

As shown in Table 4 and FIGS. 3 and 4, the hemolysis reagent composition prepared in Comparative Example 1 exhibited relatively low reaction sensitivity to the total hemoglobin. In contrast, the hemolysis reagent compositions prepared in Examples 1-3, and Comparative Examples 5 and 8 exhibited excellent reaction sensitivity to the total hemoglobin.

Experimental Example 4

Evaluation of Reactivity Between Surfactant and Substrate

Generally, an accurate quantification of a substrate can be obtained when the substrate develops a color by a reaction between hydrogen peroxide produced as a result of an enzyme reaction and a peroxidase. Therefore, the color development between a surfactant and a substrate may generate errors in the quantitative analysis. In this regard, the reactivity between surfactants and substrates were examined by the experiments performed as follows.

More specifically, the absorbances of the hemolysis reagents prepared in Examples 1-3 and Comparative Examples 1, 2, 4, 5 and 8 were analyzed by the UV/Vis device used in Example 2 instead of reacting the hemolysis reagents with blood samples.

The result revealed that all surfactants included in the hemolysis reagents prepared in Examples 1-3 and Comparative Examples 1, 2, 4, 5 and 8 did not react with substrates thus confirming that they are suitable for the use of quantitative analysis.

Experimental Example 5

Evaluation of Reaction Sensitivity and Reaction Rate of HbA1c

In performing quantification of the HbA1c via an enzymatic method, it is important that the reaction sensitivity to the HbA1c be excellent. In this regard, the effect of the hemolysis reagent compositions prepared according to the present invention on the reaction sensitivity of the HbA1c and the rate of hemolysis reaction was examined by the experiments described below.

More specifically, regarding the reaction sensitivity, four blood samples with different HbA1c concentrations (72 μM, 120 μM, 152 μM, and 264 μM) were prepared, and each of the blood samples were reacted for 1 minute with the hemolysis reagent compositions prepared in Examples 1-3 and Comparative Examples 1, 2, 4, 5 and 8, respectively, by mixing them in a ratio of 1:400 (blood:hemolysis reagent), subsequently reacted with a composition for enzyme reaction prepared in Preparation Example 1 for 2-3 minutes, and their HbA1c levels were measured.

The HbA1c levels were measured at 633 nm, at which DA-67 (manufactured by Wako) used as a substrate among the enzyme reaction compositions prepared in Preparation Example 1 emits a specific wavelength, using the same UV/Vis device used in Example 2, and the results are shown in Tables 5 and 6 below. Furthermore, the slope of the graphs indicating the reaction sensitivity of the HbA1c measurements in FIGS. 5 and 6 are shown in Table 5 below.

TABLE 5

| | Measurement Sensitivity of HbA1c |
|---|---|
| Ex. 1 | 0.1046 |
| Ex. 2 | 0.1062 |
| Ex. 3 | 0.0990 |
| Comp. Ex. 1 | 0.0046 |
| Comp. Ex. 2 | 0.0854 |
| Comp. Ex. 4 | 0.0583 |
| Comp. Ex. 5 | 0.0868 |
| Comp. Ex. 8 | 0.0567 |

Figure 5:
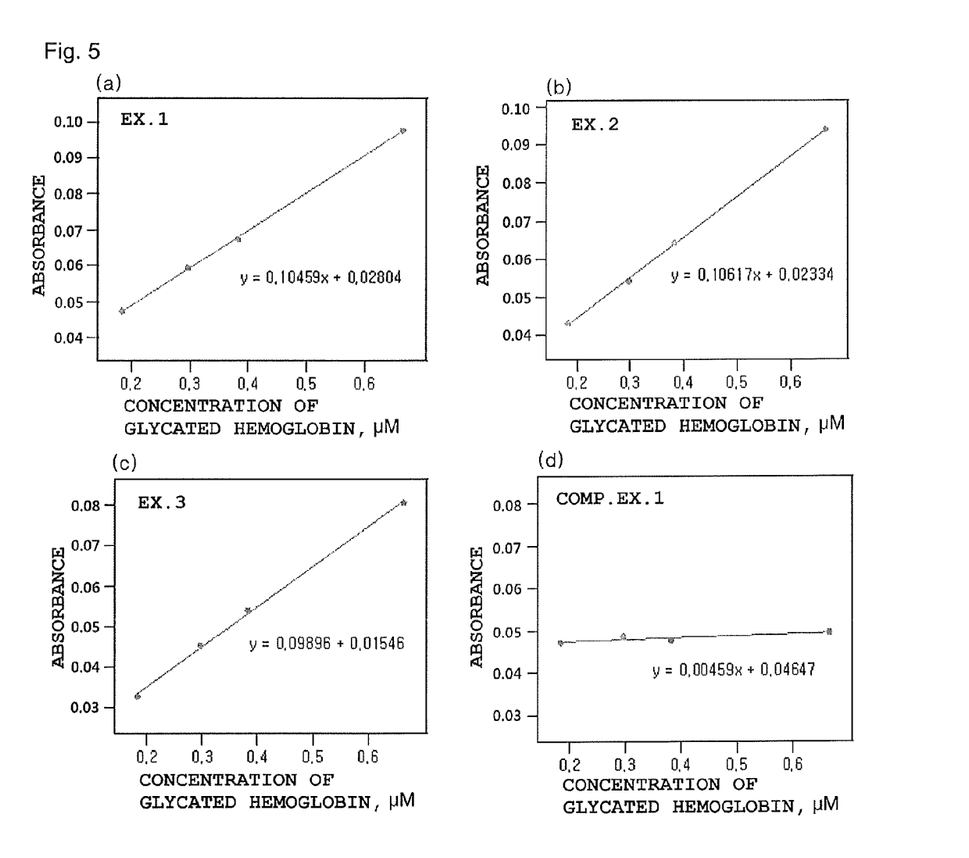
FIGS. 5(a)-5(d) show graphs representing reaction sensitivity of the hemolysis reagent compositions prepared in Examples 1-3 and Comparative Example 1 of the present invention to the HbA1c (in FIG. 5, the larger the slope the greater the reaction sensitivity and reaction rate to the HbA1c).
Figure 6:
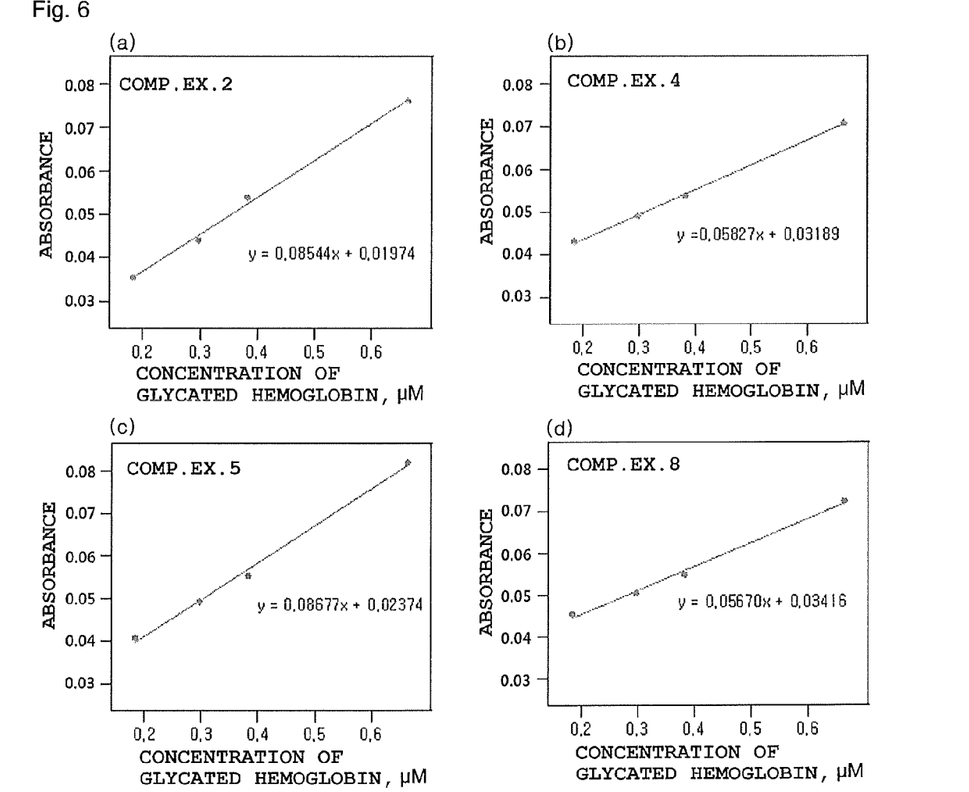
FIGS. 6(a)-6(c) show graphs representing reaction sensitivity of the hemolysis reagent compositions prepared in Comparative Examples 2, 4, 5 and 8 of the present invention to the HbA1c (in FIG. 6, the larger the slope the greater the reaction sensitivity and reaction rate to the HbA1c).

FIG. 5 shows graphs representing reaction sensitivities of the hemolysis reagent compositions prepared in Examples 1-3 and Comparative Example 1 of the present invention to the HbA1c (in FIG. 5, the larger the slope the greater the reaction sensitivity and reaction rate to the HbA1c).

FIG. 6 shows graphs representing reaction sensitivities of the hemolysis reagent compositions prepared in Comparative Examples 2, 4, 5 and 8 of the present invention to the HbA1c (in FIG. 6, the larger the slope the greater the reaction sensitivity and reaction rate to the HbA1c measurement).

Additionally, the reaction rates of the hemolysis reagent compositions on the HbA1c assays were examined by the experiments described below.

More specifically, the reaction rates were compared by the reaction sensitivity per unit hour. The reaction rates were compared based on the respective slope in each of the hemolysis reagents by setting up the total reaction time as 3 minutes, respectively. The basis that the slope can be regarded as a reaction rate in FIGS. 5 and 6 is that a reaction slope will be small because the entire reaction is slow even when any one of the two reactions of the hemolysis and the enzyme reaction.

As shown in Table 5 and FIGS. 5 and 6, the hemolysis reagent composition prepared in Comparative Example 1 showed almost no reaction sensitivity on the HbA1c within 3 minutes. In contrast, the hemolysis reagents composition prepared in Examples 1-3 showed relatively large slope valued in the calibration curves in the range of from 0.09 to 0.1. In particular, all the surfactants used in Examples 1-3 showed common molecular structures in their tail chains consisting of 14 carbons. Therefore, it is speculated that the surfactants consisting of 14 carbons in their tail chains can mediate an easy reaction between the HbA1c and an enzyme.

Experimental Example 6

Evaluation of the Effect of a Nitrous Compound on the Reaction Sensitivity of HbA1c Generally, a nitrous compound has been known as a material used for measuring the amount of the total hemoglobin. However, in the enzymatic method for measuring the level of HbA1c in the present invention, the role of the nitrous compound was examined by the experiments described below to see whether it is involved in an auxiliary action of mediating the cutting off of the sequence of the protein structure of the hemolyzed HbA1c via a protease by flexibly modifying the protein structure of the hemolyzed HbA1c, in addition to its role as an oxidizing agent.

More specifically, three blood samples with different HbA1c concentrations (52 $\mu$M, 98 $\mu$M, and 125 $\mu$M) were prepared, and then reacted for 1 minute with each of the hemolysis reagent compositions prepared in Example 1 and Comparative Example 10 (exclusive of the nitrous compound in the composition of Example 1), respectively, by mixing them in a 1:400 ratio (blood:hemolysis reagent), subsequently reacted with a composition for enzyme reaction prepared in Preparation Example 1 for 3 minutes, and their HbA1c levels were measured.

Figure 7:
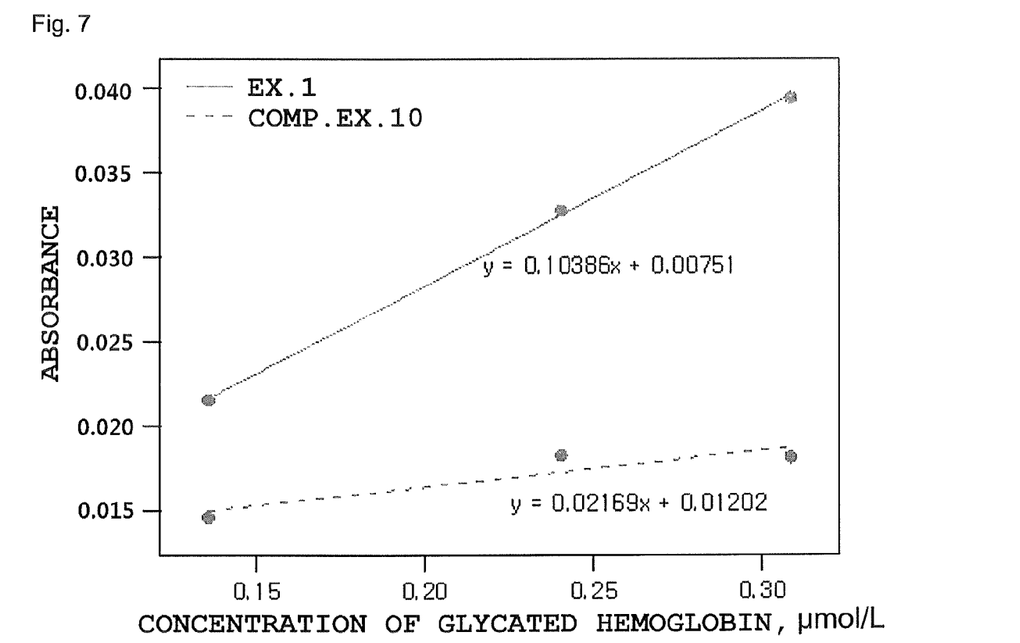
FIG. 7 shows a graph representing reaction sensitivity of the hemolysis reagent compositions prepared in Example 1 and Comparative Examples 10 of the present invention to the HbA1c (in FIG. 7, the larger the slope the greater the reaction sensitivity to the HbA1c).

The HbA1c levels were measured at 633 nm, in which DA-67 (manufactured by Wako) used as a substrate among the enzyme reaction compositions prepared in Preparation Example 1 emits a specific wavelength, using the same UV/Vis device used in Example 2, and the results are shown in FIG. 7.

FIG. 7 shows a graph representing reaction sensitivity of the hemolysis reagent compositions prepared in Example 1 and Comparative Examples 10 of the present invention to the HbA1c (in FIG. 7, the larger the slope the greater the reaction sensitivity to the HbA1c).

As shown in FIG. 7, the hemolysis reagent composition prepared in Example 1 showed its reaction sensitivity on the HbA1c (the slope of calibration curve) as 0.10386, whereas the hemolysis reagent prepared in Comparative Example 10 showed its reaction sensitivity on the HbA1c 0.02169, thus confirming that the hemolysis reagent composition of Example 1 had about 5 times bigger in the reaction sensitivity than that of Comparative Example 10. It is speculated that the protein structure of the hemoglobin is flexibly modified by the nitrous compound thereby mediating the cutting off the amino acid sequence of the N-terminal $\beta$-chain of the protease.

Experimental Example 7

Evaluation of the Effect of Surfactant on the Reaction Sensitivity of HbA1c

In order to examine the effect of the surfactants of the present invention on the reaction sensitivity of HbA1c by inducing the N-terminal $\beta$-chain of hemoglobin released by hemolysis to be exposed to the outside of the hemoglobin molecule and assisting the participation of a greater number of molecules in the reaction, experiments were performed as described below.

More specifically, four blood samples with different HbA1c concentrations (72 $\mu$M, 120 $\mu$M, 152 $\mu$M, and 264 $\mu$M) were prepared, and then reacted for 1 minute with each of the hemolysis reagent compositions prepared in Example 1 and Comparative Example 1 (exclusive of the surfactant in the composition of Example 1), respectively, by mixing them in a 1:400 ratio (blood:hemolysis reagent), subsequently reacted with a composition for enzyme reaction prepared in Preparation Example 1 for 3 minutes, and their HbA1c levels were measured.

Figure 8:
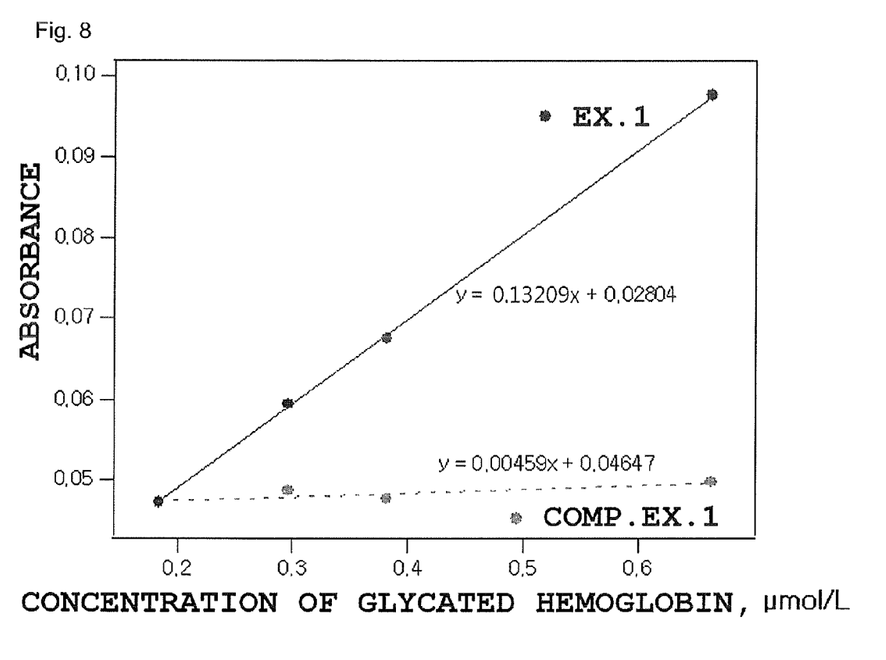
FIG. 8 shows a graph representing reaction sensitivity of the hemolysis reagent compositions prepared in Example 1 and Comparative Examples 1 of the present invention to the HbA1c (in FIG. 8, the larger the slope the greater the reaction sensitivity to the HbA1c).

The HbA1c levels were measured at 633 nm, in which DA-67 (manufactured by Wako) used as a substrate among the enzyme reaction compositions prepared in Preparation Example 1 emits a specific wavelength, using the same UV/Vis device used in Example 2, and the results are shown in FIG. 8.

FIG. 8 shows a graph representing reaction sensitivity of the hemolysis reagent compositions prepared in Example 1 of the present invention and Comparative Examples 1 to the HbA1c (in FIG. 8, the larger the slope the greater the reaction sensitivity to the HbA1c).

As shown in FIG. 8, the hemolysis reagent composition prepared in Example 1 showed its reaction sensitivity on the HbA1c (the slope of calibration curve) as 0.13209, whereas the hemolysis reagent prepared in Comparative Example 10 showed its reaction sensitivity on the HbA1c 0.00459, thus confirming that the hemolysis reagent composition of Example 1 had about 30 times bigger in the reaction sensitivity than that of Comparative Example 1. It is speculated that the result is because the zwitterionic surfactant induced the N-terminal $\beta$-chain of hemoglobin released by hemolysis to be exposed to the outside of the hemoglobin molecule and assisting the participation of a greater number of molecules in the reaction.

INDUSTRIAL APPLICABILITY

The hemolysis reagent compositions of the present invention containing a zwitterionic surfactant and a nitrous compound considerably accelerate the hemolysis rate due to the presence of the zwitterionic surfactants, and also induce the N-terminal β-chain of hemoglobin released by hemolysis to be exposed to the outside of the hemoglobin molecule and assists the participation of a greater number of molecules in the reaction, thereby improving the reaction sensitivity and reaction rate of the HbA1c, and the nitrous compound makes the protein structure of the hemoglobin flexibly modified so that the amino acid sequence of the N-terminal β-chain of hemoglobin can be readily cut off, thereby significantly reducing the entire time required for the measurement and improving the accuracy of the measurement, and thus can be used as a hemolysis reagent composition for quantitative analysis of the HbA1c.

The invention claimed is:

1. A hemolysis reagent composition for use in a pretreatment process of quantitative analysis of glycated hemoglobin via an enzymatic method comprising:
   (a) a nitrous compound and
   (b) a zwitterionic surfactant, represented by the Chemical Formula 1 below;

(Chemical Formula 1)

wherein $R^1$ and $R^2$ are independently a linear or branched $C_{1-5}$ alkyl, respectively;
n is an integer from 1 to 6;
X is a single bond or wherein when X is m is an integer from 1 to 3, and when X is a single bond m is 1; and
$R^3$ is a $C_{13}$ linear or branched alkyl.

2. The hemolysis reagent composition as set forth in claim 1, wherein $R^1$ and $R^2$ are independently a $C_{1-3}$ linear or branched alkyl, respectively:
n is an integer from 1 to 4;
X is a single bond or wherein when X is m is an integer from 1 to 3, and when X is a single bond m is 1; and
$R^3$ is a $C_{13}$ linear or branched alkyl.

3. The hemolysis reagent composition as set forth in claim 1, wherein the zwitterionic surfactant represented by the Chemical Formula 1 is selected from the group consisting of:
3-(dimethyl(3-tetradecanamidopropyl)ammonio)propane-1-sulfonate;
4-(dimethyl(3-tetradecanamidopropyl)ammonio)butane-1-sulfonate; and
3-(dimethyl(tetradecyl)ammonio)propane-1-sulfonate.

4. The hemolysis reagent composition as set forth in claim 1, wherein the nitrous compound is at least one nitrite compound selected from the group consisting of: sodium nitrite, potassium nitrite, magnesium nitrite, and calcium nitrite.

5. A method for quantitative analysis of glycated hemoglobin, comprising:
   (i) hemolyzing red blood cells using the hemolysis reagent composition of claim 1;
   (ii) measuring the total amount of hemoglobin released by the hemolysis of the red blood cells in step (i);
   (iii) obtaining monomeric fructosyl amino acids by selectively cutting off only the sugar-Val-His-moiety of the N-terminal β-chain of the glycated hemoglobin released by the hemolysis of the red blood cells in step (i) using one or more protease;
   (iv) producing hydrogen peroxide by reacting fructosyl peptide oxidase (FPOX) with the monomeric fructosyl amino acids obtained in step (iii);
   (v) oxidizing the hydrogen peroxide produced in step (iv) by reacting with peroxidase (POD);
   (vi) measuring the amount of color development induced by a redox reaction due to the hydrogen peroxide oxidized in step (v) and a substrate; and
   (vii) quantitating the concentration of the glycated hemoglobin in a blood sample by comparing the total amount of hemoglobin measured in step (ii) and the amount of the glycated hemoglobin in step (vi).

6. The method as set forth in claim 5, wherein each of the one or more proteases is selected from the group consisting of a *Bacillus* sp. protease, an *Aspergillus* sp. protease, a *Streptomyces* sp. protease, and a protease obtained from a genetic recombination thereof.

7. The method as set forth in claim 5, wherein the total amount of hemoglobin in step (ii) and the amount of the glycated hemoglobin in step (vi) are measured optically.

8. The method as set forth in claim 5, wherein the zwitterionic surfactant accelerates the hemolysis rate of red blood cells and improves enzyme activity.

9. The method as set forth in claim 5, wherein the nitrous compound improves protease activity by flexibilizing the protein structure of hemoglobin.

* * * * *